United States Patent [19]

Letsinger

[11] Patent Number: 4,786,724
[45] Date of Patent: Nov. 22, 1988

[54] NUCLEOSIDE TRICHLORODIMETHYLETHYL PHOSPHITE ESTERS

[75] Inventor: Robert L. Letsinger, Wilmette, Ill.

[73] Assignee: Northwestern University, Evanston, Ill.

[21] Appl. No.: 758,681

[22] Filed: Jul. 25, 1985

Related U.S. Application Data

[63] Continuation-in-part of Ser. No. 659,645, Oct. 11, 1984, Pat. No. 4,672,110, which is a continuation of Ser. No. 556,619, Nov. 29, 1983, abandoned.

[51] Int. Cl.$^4$ .................... C07H 19/10; C07H 19/20; C07H 19/207
[52] U.S. Cl. ........................ 536/27; 536/28; 536/29
[58] Field of Search ............................ 536/27, 28, 29

[56] References Cited

U.S. PATENT DOCUMENTS 4,419,509  12/1983  Hsiung ................................. 536/27
4,458,066  7/1984  Caruthers et al. .................... 536/27

OTHER PUBLICATIONS

Letsinger et al., "Jour. Amer. Chem. Soc.", vol. 104, 1982, pp. 6805-6806.
Eckstein, "Chem. Abst.", vol. 64, 1966, p. 3662a.
Koester et al., "Chem. Abst.", vol. 94, 1981, p. 140092x.
Kellner et al., "Chem. Abst.", vol. 95, 1981, p. 98203c.

Primary Examiner—Ronald W. Griffin
Assistant Examiner—Jenny Toll
Attorney, Agent, or Firm—Tilton, Fallon, Lungmus & Chestnut

[57] ABSTRACT

Novel trichlorodimethylethyl phosphite esters are utilized as intermediates in a new synthesis procedure for producing oligonucleotides. On completion of the synthesis the trichlorodimethylethyl protecting group can be cleaved by reaction with tributylphosphine or hexamethylphosphoramide.

6 Claims, No Drawings

NUCLEOSIDE TRICHLORODIMETHYLETHYL PHOSPHITE ESTERS

RELATED APPLICATIONS

This application is a continuation-in-part of my copending application Ser. No. 659,645, filed Oct. 11, 1984, U.S. Pat. No. 4,672,110 which was a continuation of my application Ser. No. 556,619, filed Nov. 29, 1983, abandoned.

FIELD OF INVENTION, BACKGROUND AND PRIOR ART

The field of this invention s the synthesis of polynucleotides, particularly as carried out on insoluble supports (viz. a silica support). More specifically, the invention is concerned with phosphite triester chemistry as a means for rapid synthesis of oligonucleotides.

I have recently reviewed the state of the art with respect to the phosphite triester chemistry in the synthesis of oligodeoxyribonucleotides. For general background, reference may be had to this article. See *Genetic Engineering,* Vol. 5, Ed. Setlow & Hollaender, Plenum Press, 1983, pp. 191–207. In the current methodology, the problem is that $CH_3OPCl_2$ is not highly selective in reaction with the 3'—OH of a protected nucleoside. As a consequence preparations of the active reagent yield mixtures containing the desired materials, 3'–3' coupled products (inert in the subsequent reaction), and unreacted $CH_3OPCl_2$, which must be removed from the mixture by distillation or precipitation procedures, which are troublesome to carry out with these highly moisture-sensitive materials.

There has been a need for a more selective protecting group in reacting with the nucleoside derivatives. There has also been a need for more stable intermediates.

The trichlorodimethylethyl ester group has heretofore been employed for special purposes in the synthesis of oligonucleotides. See Koster et al., *Nucleic Acids Symp. Ser.* (1980) No. 7:39–60; and Kellner et al., *Angew, Chem. Int. Ed Engle.* (1981) 20 (617):577–578. However, this group has not heretofore been employed as an ester group for protecting nucleosides in which the phosphorus bridge is in phosphite ($PO_3$) form, as distinguished from the phosphate ($PO_4$) form.

SUMMARY OF INVENTION

This invention is concerned with novel nucleotide trichlorodimethylethyl phosphite esters which can be employed to greatly facilitate olignucleotide synthesis on solid supports. The phosphite coupled monomers and dimers are very stable when the phosphite group is protected by a trichlorodimethylethyl group. This makes it possible to market such compounds in prepared form.

The novel nucleoside compounds of the present invention can be represented by the following structural formula:

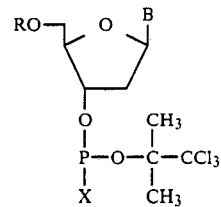

In the above formula, the designation Nuc refers to a nucleoside, which may be a deoxyribonucleoside or a ribonucleoside. Because of their value in synthesizing DNA, the preferred nucleosides are thymidine, deoxyadenosine, deoxyguanosine, and deoxycytidine. In the general formula, the letter X represents either chlorine (Cl) or —O—Nuc. As is standard practice in the synthesis of oligonucleotides, the nucleosides are protected from chemical reaction at their —OH and —$NA_2$ sites. A great variety of protecting groups for the amino and hydroxyl groups are known, but the standard protecting groups are p, p'-dimethoxytrityl (for 5'-hydroxyls); and acyl (for amino). See Schaller, et al (1963), *J. Am. Chem. Soc.* 85, 3821–3827; and Weber et al (1972), *J. Mol. Biol.* 72, 219–249. Where the compounds contain two nucleosides, they may be the same or different. Preferably, one of the nucleosides is connected through its 3' O and the other through its 5' O.

The novel nucleoside dimers are represented by the following formula:

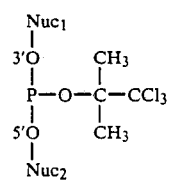

In the above formula, $Nuc_1$ and $Nuc_2$ are nucleosides connected respectively to the phosphorus through their 3' and 5' oxygens. It will be understood that the —OH and —$NH_2$ sites may be protected as described above. However, in one preferred embodiment the hydroxyl and amino sites of the $Nuc_1$ are protected, but for the other nucleoside ($Nuc_2$), only the —$NH_2$ site is protected, the hydroxyl being available for reaction. As previously described the nucleosides may be the same or different, and are preferably deoxyribonucleosides, being selected from deoxythymidine, deoxycytidine, deoxyadenosine, and deoxyguanosine.

DETAILED DESCRIPTION

The nucleoside trichlorodimethylethyl phosphotriesters of this invention can be considered in more detail with reference to the following Formulas A and B. Formulas C and D illustrate phosphate oxidized forms of the phosphite compounds of Formulas A and B.

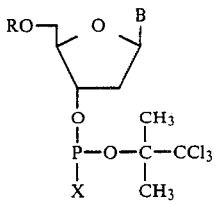
A

In Formula A, X is Cl or a related departing group such as

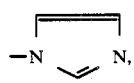

R is a conventional O-protecting group (such as $(CH_3OC_6H_4)_2(C_6H_5)C-$) and B is a purine or pyrimidine base (such as Thy, Cyt, Gua, Ade) appropriately protected at $-NH_2$ (e.g., by benzoyl or isobutyryl).

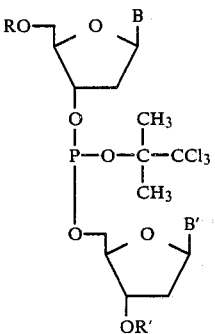
B

In Formula B, R and R' may be H or an O-protecting group and B and B' may be the same or different purine or pyrimidine bases with or without N-protecting groups.

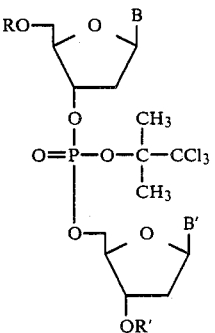
C

In Formula C, R and B and B' have the same meaning as in Formula B.

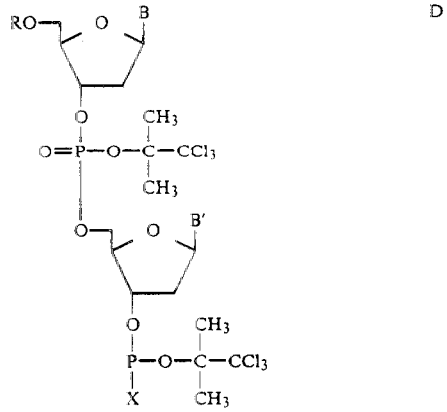
D

In Formula D, R, B, B' and X have the same meaning as in Formulas A and B.

The importance and usefulness of the compounds represented above will now be discussed in detail.

1. Compounds of type A are useful intermediates for the chemical synthesis of defined polynucleotides. The novel feature is the trichlorodimethylethyl protecting group for P-O at the trivalent oxidation stage for phosphorus. Use of this protecting group confers two advantages relative to groups previously employed.

(a) Intermediates of type A can be prepared easily in a form ready for use in polynucleotide synthesis simply by mixing solutions of protected nucleosides with solutions of $Cl_2POR$ where $R=-C(CH_3)_2CCl_3$. When conventional P-O protecting groups ($R=-CH_3$, $-C_6H_4Cl$, and $-CH_2CCl_3$) are used, the reaction of $Cl_2POR$ with the nucleoside is less selective and considerable work has to be done to obtain a reagent free from contaminants, such as residual $Cl_2POR$. As a consequence it is less expensive to synthesize a polynucleotide via intermediate A than from corresponding intermediate utilizing $-CH_3$, $-C_6H_4Cl$, or $-CH_2CCl_3$ protecting groups. Likewise, fewer synthetic operations are required than for syntheses utilizing methyl or cyanoethyl protecting groups and phosphoramidites, intermediates employed industrially at present.

(b) Use of compounds of type A afford triester derivatives (compounds of type C) which are more stable to nucleophiles than analogous compounds with conventional P-O protecting groups ($-CH_3$, $-C_6H_4Cl$, $-CH_2CCl_3$ and $-CH_2CH_2CN$). Therefore, chances for advantitious cleavage of the oligomer chains in the course of the synthetic sequence are less, a property which should lead to syntheses of longer polynucleotide chains than can be realized in procedures utilizing other protecting groups. In addition the enhanced stability of the intermediates enables one to remove phosphotriester derivatives from insoluble supports (now used commonly in synthesizing polynucleotides chemically) without loss of the P-O protecting group (a reaction which occurs with phosphotriesters with $-CH_3$, $-C_6H_5Cl$, $-CH_2CCl_3$, or $-CH_2CH_2CN$ groups) when treated with ammonium hydroxide. I have demonstrated this feature by the synthesis and isolation of a thymidine hexanucleotide derivative fully protected at all P-O links by trichlorodimethylethyl groups. This finding opens the possibility of using automated support syntheses to prepare protected fragments which can be removed from the support, purified, and then used in solution or solid phase syntheses to make long polynucleotide chains; or, in conjunction with use of other conventional protecting groups to prepare oligonucleotide analogs with the bulky trichlorodimethylethyl group at predesignated sites along the backbone.

2. Phosphite dimers of type B have unusual stability because of steric hindrances due to the bulky 2,2,2-trichloro-1,1-dimethylethyl protecting group. In addition, they can be prepared readily in solution by the following reaction:

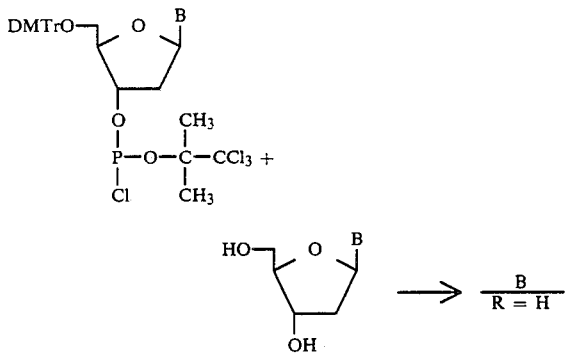

The reaction is easy to carry out and does not require protection at the B'—OH of the nucleoside component since the desired product predominates and can readily be separated from side products arising from condensation at the 5'—OH. Compound B can be converted essentially quantitatively to phosphotriester compounds of type C by oxidation with iodine-water. Similarly, by conventional reactions of phosphites it can be converted to dinucleotide analogues (e.g., by oxidation with sulfur to

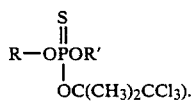

The relatively high stability of the phosphite intermediates bearing a trichlorodimethylethyl ester group opens the possibility of synthesizing long oligomer chains with phosphite internucleoside links. Such compounds could be of interest in their own right as intermediates to novel polynucleotide chains. Alternatively, the phosphite oligomers could be oxidized on the support in a final step to yield derivatives which could be carried on in the usual fashion to give the desired oligonucleotide. This route would have the advantage of requiring only one oxidation step, thereby eliminating the requirement for oxidation at each cycle.

3,4. The value of the dimer derivatives, C and D, lies in the ease of preparing these compounds in quantity in solution phase reactions and in the use of the D dimers as building blocks for synthesizing defined oligonucleotides on insoluble supports. C is prepared in a one-pot reaction sequence involving successive addition of $Cl_2POC(CH_3)_2CCl_3$, an N-protected nucleoside, and iodine-water to a 5'-O-dimethoxytrityl-N-protected nucleoside. Use of A and B as intermediates provides a more convenient route to dimer B than use of pentavalent phosphorus intermediates. Compound C, in turn, can be converted to D just as A is prepared from a protected nucleoside. We have found that dimer blocks of type D react just as efficiently as monomer units of type A. This chemistry therefore should enable one to double the length of polynucleotide chains which can be synthesized by stepwise phosphite procedures.

5. The reaction of phosphines with trihaloethyl phosphotriesters is a new reaction which makes the approach of using trihaloethyl P-O protecting groups in oligonucleotide synthesis compatible with syntheses conducted on insoluble supports. The chemistry is illustrated by the following equation, where

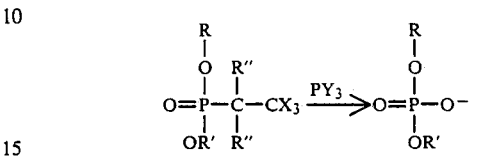

R,R' can be nucleoside units R'' can be H or $CH_3$, X can be Cl or Br, and Y can be alkyl (e.g., butyl) or —$N(CH_3)_2$. I have demonstrated that this elimination reaction proceeds cleanly in solution (dimethylformamide is a good solvent, although others also are satisfactory). With R''=H and X=Br, the reaction is rapid at room temperature. With R=H or $CH_3$ and X=Cl, the reaction is slow at room temperature (twenty four hours or more required) but is complete in less than three hours at 80° C.

With this chemistry polynucleotide trichlorodimethylethyl phosphotriester derivatives can be synthesized conveniently on insoluble supports, using monomer (A) or dimer (D) building blocks. The triesters are then converted to the corresponding phosphodiesters in one step by treatment with tributylphosphine (in dimethylformamide containing some triethylamine) and the polynucleotides are cleaved from the support and are purified by conventional procedures.

It may be noted that conventional agents for deprotecting trichloroethyl phosphotriesters such as zinc or aromatic radical-anions do not cleave phosphotriesters when bound on insoluble supports.

Experimental Procedures

1. Reagents of type A. Considerable latitude exists in choice of solvents and conditions for preparing these reagents. I have used pyridine, acetonitrile, methylene chloride and mixtures of these solvents with equal success. The essential features are that the solvents be dry and free of functional groups, such as OH, NH, COOH, that react with the active phosphorous reagents. Similarly, the order of mixing reagents is not critical. It is important however, that the nucleoside component be present in a slight molar excess relative to the $Cl_2POC(CH_3)_2CCl_3$ in preparing reagents for use in syntheses on insoluble supports in order to insure absence of the dichloridite in the subsequent coupling steps.

Details for a representative preparation are described below.

Reagents. Dichloromethane (Reagent Grade) and pyridine (Gold Label Grade, Aldrich) are dried over Molecular Sieves (4A, Linde 1/16 pellets) in closed bottles (Pierce Chem. Co. Hypo-vials closed by Tuf-Bond Discs and aluminum seals) for at least two days before use. After a seal has been broken to remove solvent, a bottle is stored in a desiccator over phosphorus pentoxide.

Protected nucleosides (d-DMTr)T, d-(DMTr)bzC, d-(DMTr)bzA, and D-(DMTr)ibG) are available from a variety of commercial sources, e.g., Vega Biochemicals, Biosearch, applied Biosystems, American Bionuclear. Samples of these protected nucleosides are rendered anhydrous by standing in open bottles in a desiccator over phosphorus pentoxide until the weight loss is constant (about two days).

2,2,2-Trichloro-1,1-dimethylethyl phosphorodichloridite ($Cl_3CC(CH_3)_2OPCl_2$) can be prepared by dehydration of 1,1,1-trichloro-2-methyl-2-propanol hydrate ($Cl_3CC(CH_3)_2OH.H_2O$) by azeotropic distillation of toluene followed by refluxing (15 hours) with excess phosphorus trichloride (two moles per mole of the alcohol) and vacuum distillation. See Gerrard et al, Research (Landon) 949, 2, 536.

Special Equipment. Two syringes. For the small scale described here, 1 mL syringes equipped with 3" removable needles and Teflon plungers (Glencoe Scientific Co.) work well. One is used in transferring nucleoside solutions; the other, in synthesis of the oligonucleotides. The latter is fitted at the base with a tightly fitting polyethylene filter disc cut from a commercial filter (Ace Glass Inc.) or with a plug of glass wool.

Four test tubes (~10 mL capacity; 6.5 cm long is convenient) for use in preparing the nucleoside phosphorochloridite reagents. Each s closed by a septum and provided with a small drying tower consisting of a plastic, disposable syringe filled with Indicating Drierite. These towers serve to dry air and equalize pressure when solvents are added or withdrawn or the temperature is changed.

Preparation of Nucleoside Phosphoromonochloridite Reagents (A). The procedure is illustrated by the preparation of

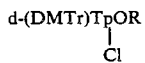

from 200 μmole of d-(DMTr)T, which yields enough active reagent for about ten cycles of synthesis on the scale described here (1.3 μmole of nucleoside initially bound to the support). The other nucleoside reagents are made in the same manner. All vessels containing dry solvents are closed by septa, and liquid transfers are effected by syringe.

Dry d-(DMTr)T (109 mg, 200 μmole is weighed into a dry test tube or vial. The tube is closed by a septum and dry dichloromethane (0.8 mL) and pyridine (0.2 mL) are added.

To a dry reaction tube equipped with a magnetic stirring bar, septum, and pressure equalizing tower is added 0.1 mL of dry pyridine and 0.61 mL of a stock solution of $Cl_3CC(CH_3)_2OPCl_2$ in dry dichloromethane (1:19 v/v; 170 μmoles of the dichloridite). The tube is cooled with a Dry Ice/i-propyl alcohol bath (−78° C.); then the solution containing d-DMTr)T is added via syringe over a period of ten minutes. Good mixing is maintained by a magnetic stirrer. To achieve quantitative transfer of the nucleoside, the tube that held the nucleoside is rinsed twice with 0.2 mL portions of dry dichloromethane and the rinsings are added to the reaction flask. After an additional five minutes at −78° C. the reaction vessel is removed from the bath and allowed to warm to room temparature. If kept overnight or for longer periods, the vessel with the reagent should be stored in a closed container with a desiccant (Drierite) in a cold freezer.

An alternative procedure which is simpler operationally yet equally effective is to dissolve the nucleoside in pyridine (0.2 mL) and $CH_2Cl_2$ (0.8 mL), close the bottle or tube with a septum, and cool (using the Drierite drying towers previously mentioned or an inert atmosphere) the bottle with a Dry-Ice isopropyl alcohol bath to ~−78° C. The solution of $Cl_3CC(CH_3)_2OPCl_2$ in $CH_2Cl_2$ is then added rapidly (~1-2 seconds) and the mixture is then removed from the bath and allowed to warm to room temperature. It is then ready for use in synthesis. I have found that the dT reagent can even be prepared satisfactorily at room temperatures; however, the low temperature reaction s advantageous in the case of the dG reagent.

The activity of the phosphite reagent can be checked by adding a couple of drops to a few drops of methanol on one hand, and to a few drops of 1:10 water/acetonitrile on the other. On thin layer chromatography (Eastman silica, developed with ethyl acetate) and spraying with 10% perchloric acid in water, the products with dimethoxytrityl groups appear as bright orange spots. One observes a dominant spot for the methyl ester derived from active nucleoside monochloridite, followed by two weak spots corresponding to reagent that had reacted with water and to a 3'—3' coupling product. For the d-(DMTr)ibG reagent, 1-butanol is preferable to methanol as a quenching agent since the reaction products are then easier to separate chromatographically with ethyl acetate as the developing solvent. Alternatively, one may quench with methanol and use tetrahydrofuran as the developing solvent for chromatography in the case of the dG reagent. The mixture quenched by water serves as a control; it should show spots for the hydrolysis product and the 3'—3' product.

All the active reagents of type A (X=Cl) exhibit a $^{31}P$ resonance in the NMR at −177.8 ppm in tetrahydrofuran (relative to triphenyl phosphate as a standard). The samples also exhibit $^{31}P$ signals at −151.3 ppm (attributable to the 3'—3'-dinucleoside phosphite formed from the exces 5'-DMTr-nucleoside, but no signals characteristic of a phosphorodichloridite (−213 ppm) are observed.

2. Use of A reagents in Synthesizing Polynucleosides on Insoluble Supports.

The reagents can be employed in a variety of ways to give oligo- or polynucleotides. A simple manual procedure is described here. I have also used the reagents successfully in a commercial automated machine.

Silica supports. Silica supports loaded with N-acyl-5'O-dimethoxytritylnucleosides are commercially available from several sources. Much of our work has been carried out on solid samples prepared in-house from Davison 62 silica (W. R. Grace Co.; 140–200 mesh, 140 nm average pore diameter, 300 m²/g surface area) loaded to about 30 μmoles nucleoside/gram via a conventional succinylaminopropylsilyl linker (see Matteucci and Caruthers, J. Am. Chem. Soc. 103, 3185–3191 (1981). Satisfactory results have also been obtained with a crosslinked polystyrene support and a controlled pore glass support (available from Pierce Chem. Co.). Vydac silica (Biosearch Chemicals) is so fine it passes through some polyethylene filters (Ace Glass). A finer pore filter must be used in this case (e.g., Nasco, Whirl-Pac).

Many workers employ a capping step in a synthetic cycle to block any residual hydroxyl groups not attacked by the phosphite reagent. This step is not included in the present procedure; however, if desired it can readily be included by treating the loaded silica with acetic anhydride/dimethylaminopyridine/pyridine for a few minutes prior to the detritylation step.

Detritylation. A sample of silica loaded with DMTr-nucleoside (e.g., 50 mg of d-(DMTr)T silica containing 1.3 μmole of d-(DMTr)T) is weighed into the syringe functioning as the reaction vessel; then 3% trichloroacetic acid in nitromethane (~0.4 mL) is drawn into the syringe. After a minute the resulting orange solution is ejected into a 5 mL volumetric flask, and the silica support is washed repeatedly with 3% trichloroacetic acid/nitromethane until no further color develops. The volumetric flask containing the collected washings is filled to 5 mL with 3% trichloroacetic acid/nitromethane and the absorbance is read at 443 nm ($E_{min} = 6.24 \times 10^3$) to determine the concentration of dimethoxytrityl cation liberated. The silica in the syringe is washed free of trichloroacetic acid with pyridine/acetonitrile (1:4).

Synthetic Cycle for Adding a Nucleotide Unit. Bottles containing solvents and reagents for the oligonucleotide synthesis are arranged in order as indicated in Table 1. The dry pyridine and the nucleoside phosphorochloridite solutions are protected from moisture as previously described. No special precautions to exclude moisture from the other bottles are needed, but standard safety procedures should be followed to avoid escape of fumes into the room. A bottle to receive waste solutions should also be available. Synthesis is effected by successively drawing in and ejecting solutions from the syringe. The syringe should be rotated or tilted back and forth several times during this period to achieve good mixing. The chemistry occurs in steps 2, 4 and 7 (coupling, oxidation, detritylation). Step 1 dries the silica and the reaction vessel, and the remaining operations are washing steps. After step 8 the system is ready for the next cycle of synthesis. The yield for a given cycle can be estimated from the absorbance values for the dimethoxytrityl cation liberated in that cycle and the preceding cycle.

TABLE 1

Reagents and Operations for a Synthetic Cycle

| Step | Reagent | Number of Treatments |
|---|---|---|
| 1 | Dry Pyridine Or Acetonitrile | 5 |
| 2 | Nucleoside Phosphorochloridite | 1 (10 min.) |
| 3 | Acetonitrile | 5 |
| 4 | 0.1 M $I_2$ in Tetrahydrofuran/Pyridine/Water (10:5:1,v/v/v) | 1 (2 min.) |
| 5 | Acetonitrile | 3 |
| 6 | Nitromethane | 3 |
| 7 | 3% Trichloroaetic Acid in Nitromethane | Several |
| 8 | Pyridine/Acetonitrile (1:4) | 3 |

Deprotection (Cleavage with tributylphosphine). After the last synthetic cycle the silica with the attached oligonucleotide is washed with ethyl ether, dried, and poured into a small vial containing dimethylformamide (200 μL), tributylphosphine (100 μL) and triethylamine (50 μL). The vial is capped and heated at 80° C. for three hours. Liquid reagents are removed by decanting and the silica is washed twice with ethyl ether. Concentrated ammonium hydroxide (300 μL) is added, the vial is capped, and the mixture heated at 50° C. for fifteen hours. After cooling, the ammoniacal solution is collected, the silica is washed three times with small portions of water, and the combined solutions are lyophilized. The residue is taken up in water and freed of residual silica by centrifugation. The polynucleotide is then isolated from the aqueous medium by standard procedures, e.g., silica get chromatography (see Tanaka and Letsinger, Nucleic Acids Research 10, 3249–3260 (1982) or by reverse phase chromatography (see Letsinger, Groody, and Tanaka, J. Am. Chem. Soc., 104, 6805–6806 (1982)).

This procedure was used to deprotect a synthetic oligomer phosphotriester on a silica support in the preparation of d-GCAAATATCATTTT (J. Am. Chem. Soc. 104, 6805–6806 (1982)). In developmental work with dinucleotide triesters in solution phase, it was found that triphenylphosphine did not react with the trichloroethyl phosphotriesters; however, the reaction proceeded smoothly at a good rate at 80° C. in a mixture of tributylphosphine, dimethylformamide, and triethylamine (2/4/1, v/v/v), affording 95% or more of the phosphodiester cleavage product duct (by TLC analysis) within an hour. No side reactions involving the base rings were detected in control experiments with d-bzC, d-bzA, d-iBG, and dT. The course of the reaction was confirmed by isolating the nucleotide products from the cleavage of representative compounds. For this purpose dimer or tetramer trichlorodimethylethyl phosphotriester derivatives were heated (80° C.) for 2 hours with the tributylphosphine, dimethylformamide, triethylamine mixture, and after cooling, the nucleotide products were precipitated by adding ether/pentane (3/2). N-protecting groups were removed by NH4OH and the nucleosides purified by HPLC on a reverse phase column. Products and yields were: d-AA (70%), d-CC (60%), d-GC (73%), d-AATT (60%), and d-TTAA (84%).

3. Synthesis of Phosphite Reagents of Type B. This synthesis is illustrated by preparation of 2,2,2-trichloro-1,1-dimethylethyl 5'O-Mono-p-methoxytritylthymidyl-3'thymidyl-5' phosphite (R=MTr, R'=H, B=B'=thymine). 5'O-Mono-p-methoxytritylthymidine (d-MMTr)T (145 mg, 0.28 mmol) in THF/pyridine (0.9 mL, 2/1, v/v) was added dropwise (10 min) to a stirred solution of Cl₃CC(CH₃)₂OPCl₂ (80 mL, 0.44 mmol) at −78° C. The empty flask was rinsed with THF/pyridine (0.6 mL) and the rinsings added to the reaction mixture. After 15 min, thymidine (174 mg, 0.72 mmol) in THF/pyridine (2.9 mL, 5/3, v/v) was added. The mixture was stirred 15 min at −78° C. and warmed to 0° over a 15 min period. Dilution with CH₂Cl₂ (100 mL), extraction with NH4OH (50 mL), concentration of the CH₂Cl₂ layer and chromatography (silica plate CHCl₃/CH₃OH (10/1) gave the title compound, isolated by elution with CHCl₃ and precipitated by dropwise addition of the CHCl₃ solution (2 mL) into pentane (25 mL); 189 mg (70%) ³¹P NMR (THF) −151.3, 151.0 ppm. Rf (CHCl₃/CH₃OH 10/1) 0.48.

Anal. Calcd. for $C_{44}H_{48}Cl_3N_4O_{12}P$: C, 54.92; H, 5.04; N, 5.82. Found: C, 54.92, H, 4.82, N, 5.72.

Oxidation (2 mg, Rf 0.23 on reverse phase TLC, acetone/H₂O, 7/3) with I₂/THF/H₂O, showed complete conversion to the phosphate (C), Rf 0.43 on reverse phase thin layer chromatograph, using acetone/H₂O, 7/3.

4. Synthesis of Phosphotriester Dimer Blocks of Type C. This chemistry is represented by the synthesis of dimer C in which R=mono-p-methoxytrityl (MTr), R'=H, and B=B'=thymine. The preparation of B was repeated. At the stage the mixture had warmed to 0° C., the phosphite was oxidized by addition of excess iodine in THF/H₂O (3 mL, 2/1). After 40 min, excess iodine was reduced with aqueous Na₂S₂O₃ (sufficient added to convert the dark brown solution to pale yellow); then the product was worked up as in the case of phosphite B to give 149 mg of C (54%); $^{31}$P NMR (THF) −10.36, −10.23 ppm. Rf silica (CHCl$_3$/CH$_3$OH, 10/1) 0.42; Rf reverse phase (acetone/H$_2$O, 7/3) 0.43.

Anal. Calcd. for C$_{44}$H$_{48}$Cl$_3$NH$_4$O$_{13}$P: C, 54.02; H, 4.95; N, 5.73. Found: C, 53.69; H, 5.06; N, 5.62.

Dimer blocks of other nucleosides were prepared in the same manner except for dimers containing d-ibG as the 3'-terminal nucleoside. In this case, for solubility reasons, the d-ibG is dissolved in dry dimethylformamide/pyridine rather than tetrahydrofuran/pyridine.

Detritylation of C; [2,2,2-Trichloro-1,1-dimethylethyl Thymidyl-3' Thymidyl-5 = Phosphate]. For further characterization compound C (R = MTr, R' = 1, B = B' = thymine) was detritylated by dissolving in 80% aqueous acetic acid. After 12 hours, the product was recovered by concentrating the solution under vacuum, adding pyridine, concentrating the pyridine solution, and then precipititating by dropping the concentrated pyridine solution (1 mL) into ether (20 mL). The precipitate was the desired title compound. Yield, 31.4 mg (85%); $^{31}$P NMR (THF/pyridine, 8/2) −10.30 ppm; Rf reverse phase (acetone H$_2$O 7/3) 0.85.

Anal. Calcd. for C$_{24}$H$_{32}$Cl$_3$N$_4$O$_{12}$P.H$_2$O: C, 39.81; H, 4.85; N, 7.78. Found: C, 39.85; H, 4.85; N, 8.11.

5. Use of Dimer Blocks of types C and D in Synthesis of Oligonucleotide Phosphotriesters in solution Phase. Data on yields and properties are summarized in Table 2. Dimer units of type C were prepared essentially by the procedure described in section 3. Thus dimer units d(DMTr)TpT (7) (70%) and d-(DMTr)bzApbzA (13) (45%) were prepared as described, except that the ratio of d-DMTr-nucleoside/Cl$_3$CC(CH$_3$)$_2$OPCl$_2$/nucleoside was 1.0/1.3/2.0. Compound 9 was prepared by acetylation of 7 (101 mg; 0.2 mL acetic anhydride and 0.1 g p-dimethylaminopyridine in 1.33 mL THF, 0.36 mL pyridine, 10 min) followed by detritylation with 80% aqueous acetic acid (1 h, r.t.). d-bzApbzA(OAc), 14, was similarly prepared from 13, except that detritylation was effected with C$_6$H$_5$SO$_3$H (30 mg) in CHCl$_3$/CH$_3$OH (6 mL; 7/3) at 0° for 10 min. All products were purified by chromatography on silica plates. The product band was eluted with CH$_3$OH, and after evaporation the residue was taken up in CHCl$_3$ (1 mL) and precipitated in pentane (20 mL).

A reagent of type D (R = DMTr, X = Cl, B = thymine) used in dimer coupling, was prepared by adding 7 (504 mg, 0.5 mmol) in THF/pyridine (1 mL, 1/1) to Cl$_3$CC(CH$_3$)$_2$OPCl$_2$ (137 mL, 0.75 mmol) in THF/pyridine (1.5 mL, 2/1) at −78° C. After 20 min at −78° the mixture was centrifuged and the supernatant dropped into pentane (40 mL) with stirring. After settling, pentane was removed from the precipitate by syringe. The residue was washed with pentane and taken up in THF (1.5 mL) and pyridine (0.5 mL). Care was taken to keep moisture away from the active reagent at all times. Activity was tested by adding a small portion of the solution to CH$_3$OH on one hand and H$_2$O on the other. Conversion to the methyl ester (~80%; Rf 0.8 in EtOAc on silica) with only a minor amount of hydrolysis product (Rf 0.5) indicated high conversion of 7 to the active phosphite reagent (D).

The corresponding deoxyadenosine derivative, d-(DMTr)bzApbzAPCl—OC(CH$_3$)$_2$CCl$_3$, was similarly prepared in ~60% yield from 13 (164 mg) and Cl$_3$CC(CH$_3$)$_2$OPCl$_2$The Rf of the methyl ester obtained on reaction with methanol was 0.71 (silica, EtOAc).

Block couplings were accomplished by treating the appropriate 5'—OH, 3'OAc derivative with 2 equivalents of the 5'DMTr−3'O-phosphorochlorodite reagent in THF/pyridine (2/1) at room temperature for 10 min, then with excess iodine in THF/H$_2$O (2/1) for 40 min to oxidize the phosphite. Products were worked up in the usual manner, and were isolated by chromatography on silica plates.

6. Demonstration of Removal of Oligomers from a Solid Support with the 2,2,2-Trichloro-1,1-dimethylethyl Phosphotriester Groups Intact. In some cases it could be advantageous to have the capability of removing oligonucleotide derivatives from a solid support with all or some of the potentially labile triester links intact. With current methodology, methyl, chlorophenyl, and trichloroethyl are not suitable protecting groups for P-O for such applications since they are sensitive to the ammoniacal conditions used to sever the acyl functions holding the oligomers to the solid support. The finding that nucleoside trichlorodimethylethyl phosphotriesters are relatively stable to ammonium hydroxide provides a way around this difficulty. To illustrate the feasibility of recovering oligonucleotide triesters from a solid support we synthesized a hexathymidylate derivative on silica.

The synthetic cycles were carried out by previously described procedures with compound A (R = dimethoxytrityl, R' = Cl, B = thymine) as the active phosphite reagent. At each stage, samples of the loaded silica were removed for recovery of oligomers. Pertinent data on the course of the synthesis are collected in Table 3. Yields based on the trityl cation liberated in the detritylation step averaged a little over 80% per step. Samples

TABLE 2

| Product | Block Synthesis in Solution Nucleotide Precursors | % Yield | Rf$^a$ | Rf$^b$ |
|---|---|---|---|---|
| d-(DMtr)TpT, 7 |  | 70 | .36 | .54 |
| d-(HO)TpT(OAc), 9 | 7 | 76 | .31 | .75 |
| d-(DMTr)(Tp)$_3$T(OAc), 10 | 7, 9 | 93 | .39 | .34 |
| d-(DMTr)(Tp)$_3$T, 10a | 10 | 81 | .20 | .43 |
| d-(HO)(Tp)$_3$T(OAc), 11 | 10 | 89 | .24 | .59 |
| d-(DMTr)(Tp)$_5$T(OAc), 12 | 7, 11 | 81 | .31 | .28 |
| d-(DMTr)(Tp)$_5$T, 12a | 12 | 89 | .20 | .33 |
| d-(DMTr)bzApbzA, 13 | d-(DMTr)bzA d-bzA | 62 | .40 | .34 |
| d-bzApA)(OAc), 14 | 13 | 73 | .48 | — |
| d-(DMTr)(bzAp)$_2$TpT(OAc), 15 | 13, 9 | 71 | .49 | .26 |
| d-(DMTr)(Tp)bzApbzA(OAc), 16 | 7, 14 | 70 | .48 | .23 |

$^a$TLC, silica, CHCl$_3$/CH$_3$OH 10/1.
$^b$TLC, RP (C-18), Acetone/H$_2$O 7/3. In the notation for nucleotide derivatives, p refers to the internucleoside link —O—P(O)O—C(CH$_3$)$_2$CCl$_3$.

of oligomers removed by treating the silica with ammonium hydroxide (4 h, 25° C.) were analyzed by thin layer chromatography (TLC) and by high performance liquid chromatography (HPLC). In each case a major band corresponding to the expected d-(DMTr)(Tp)nT was obtained. The HPLC bands were broad, reflecting stereoisomers at phosphorus. The hexamer recovered from a cut of the main band corresponded to 15% of the initial thymidine units on the silica gel. On deblocking with zinc, it afforded d-(DMTr)TTTTTT, which appeared as a sharp peak on HPLC.

TABLE 3

Products from Synthesis of d-(DMTr)(Tp)$_n$T on Silica.

| n | % Yield[a] | Rf, TLC[c] | Rf, TLC[b] | Elution time (min.) MeCN/H$_2$O, 1:1 | HPLC[c] 3:2 |
|---|---|---|---|---|---|
| 0 | — | 0.51 | 0.45 | 5.44 | |
| 1 | 84 | 0.32 | 0.40 | 8.08 | |
| 2 | 84 | 0.24 | 0.35 | 13.7 | |
| 3 | 80 | 0.22 | 0.29 | 22.8 | |
| 4 | 81 | 0.20 | 0.24 | 40 | 8.8 |
| 5 | — | 0.19 | 0.21 | — | 11.2 |

[a]Based on trityl cation.
[b]Silica; CHCl$_3$/CH$_3$OH 10:1.
[c]Reverse phase (C-18); acetone/H$_2$O 7.3.
[d]Whatman Partisil ODS3 column, 2 mL/min flow rate.

These experiments demonstrate that nucleoside trichlorodimethylethyl phosphotriesters are sufficiently stable to be removed from solid supports under mild ammoniacal conditions.

7. Syntheses with Dimer Blocks on Insoluble Supports. For construction of extended oligonucleotide chains on insoluble supports, synthesis with dimer blocks is advantageous. Block synthesis has been employed in the conventional triester approach, but has not been exploited with phosphite chemistry. Use of the bulky, relatively stable trichlorodimethylethyl group for protecting phosphorus enables one to prepare dimer blocks conveniently in solution and to convert them to active phosphite derivatives for syntheses on solid supports. An important question, however, concerns the efficiency of coupling dimer blocks to oligonucleotide fragments via phosphite chemistry on an insoluble support. As a test d-T$_5$ was prepared by two cycles of reaction of dimer C with d-T bound to a silica support. For this purpose dimer C (R=DMTr, B=B'==thymine) was converted to the active phosphorus (III) reagent (D) exactly as d-DMTrT was converted to active reagent A (i.e., same mole ratios, solvents, temperatures, and operational conditions). Reagent D in turn was used in the reactions with thymidine bound to the silica support just as A was used in the monomer couplings except that 20 minutes was allowed for each coupling step (step 2 in the protocol outlined in Table 1) for monomer reactions. Coupling yields by the trityl cation test were 97% and 94%. In addition, analysis by HPLC of the crude reaction mixture obtained on treating the loaded silica with ammonium hydroxide indicated very clean conversion to the expected pentamer (dTpTpTpTpT) with only very small amounts of side products produced in the synthetic and deprotection steps.

DEPROTECTION METHOD

It will be apparent from the foregoing disclosure that a novel method of deprotection is used for the phosphotriester groups which include as a protecting group a trichlorodimethylethyl group. This method can be applied while the oligonucleotide remains attached to the silica or other solid support. The reagents for the deprotection are applied in the liquid phase, and therefore may also be used for deprotection where the oligonucleotide has been removed from the support. The preferred reagent is P(C$_4$H$_9$)$_3$, tributylphosphine. However, P[N(CH$_3$)$_2$]$_3$, hexamethylphosphoramide, may be employed in a similar manner with comparable results. More generally, the two classes of reagents which can be used consist of:

(a) P-(alkyl)$_3$, and
(b) P-(N-alkyl$_2$)$_3$

In the foregoing formulas, the trialkyl groups may each contain from 2 to 6 carbons, a 4 carbon content being preferred as in tributylphosphine; and the alkyl amino groups may each contain from 1 to 4 carbons, a 1 carbon content being preferred in phosphoramidite. Instructions for use of these reagents in deprotection are contained in the foregoing specification, and specifically in the section referring to "Deprotection."

I claim:

1. The nucleoside trichlorodimethylethyl phosphite esters represented by the structural formula:

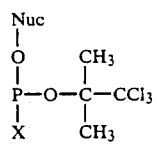

wherein X is selected from Cl and —O—Nuc and Nuc represent nucleosides which are protected at their —OH and —NH$_2$ sites.

2. The nucleoside phosphite esters of claim 1 in which X is Cl.

3. The nucleoside phosphite esters of claim 1 in which X is —O—Nuc.

4. The nucleoside phosphite esters of claim 1 in which Nuc represents nucleosides selected from the group consisting of deoxythymidine, deoxycytidine, deoxyadenosine, and deoxyguanosine.

5. The nucleoside phosphite dimers represented by the structural formula.

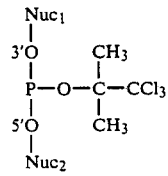

wherein Nuc$_1$ and Nuc$_2$ are nucleosides connected respectively to the phosphorus through their 3' and 5' oxygens, said Nuc$_1$ being protected at its —OH and —NH$_2$ sites, and said Nuc$_2$ being protected at only its —NH$_2$ site.

6. The dimers of claim 4 in which Nuc$_1$ and Nuc$_2$ are nucleosides selected from the group consisting of deoxythymidine, deoxycytidine, deoxyadenosine, and deoxyguanosine.

* * * * *

UNITED STATES PATENT AND TRADEMARK OFFICE
CERTIFICATE OF CORRECTION

PATENT NO. : 4,786,724

DATED : November 22, 1988

INVENTOR(S) : Robert L. Letsinger

It is certified that error appears in the above-identified patent and that said Letters Patent is hereby corrected as shown below:

Column 1, line 16, delete "s" insert --is--.

Column 2, line 26, delete "p, p'-dimethoxytrityl" insert --p, p'-dimethoxytrityl--.

Column 4, line 41, delete "mediate" insert --mediates--.

Column 7, line 25, delete "s closed" insert --is closed--.

Column 7, line 35 (first line of formula), delete "d-(DMTr)TpOR" insert --d-(DMTr)TpOR--.

Column 7, line 54, delete "Dry Ice/i-propyl" insert --Dry Ice/i-propyl--.

Column 7, line 55, delete "d-DMTr)T" insert --d-(DMTr)T--.

Column 10, line 35, delete "5'O-Mono-p-methoxytritylthymidyl-" insert --5'O-Mono-p-methoxytritylthymidyl---.

Column 10, line 37, delete "5'O-Mono-p-methoxytritylthymidine" insert --5'O-Mono-p-methoxytritylthymidine--.

Column 10, line 63, delete "R = mono-p-methoxytrityl" insert --R = mono-p-methoxytrityl---.

Column 11, line 32, delete "d(DMTr)TpT (7)" insert --d(DMTr)TpT (7)--.

Column 11, line 32, delete "d-(DMTr)bzApbzA (13)" insert --d-(DMTr)bzApbzA (13)--.

UNITED STATES PATENT AND TRADEMARK OFFICE
CERTIFICATE OF CORRECTION

PATENT NO. : 4,786,724

DATED : November 22, 1988

INVENTOR(S) : Robert L. Letsinger

It is certified that error appears in the above-identified patent and that said Letters Patent is hereby corrected as shown below:

Column 11, line 39, delete "d-bzApbzA(OAc)" insert --d-bzA$\underline{p}$bzA(OAc)--.

Column 12, line 14, delete "(DMTr)bzApbzAPCl" insert --(DMTr)bzA$\underline{p}$bzAPCl--.

Column 13, line 5, delete "d-(DMTr)(Tp)nT" insert --d-(DMTr)(T$\underline{p}$)nT--.

Column 13, Table 3:
    In subtitle delete "d-(DMTr)(Tp)$_n$T" insert --d-(DMTr)(T$\underline{p}$)$_n$T--.

Signed and Sealed this

Twenty-first Day of March, 1989

Attest:

DONALD J. QUIGG

Attesting Officer

Commissioner of Patents and Trademarks